US00PP16077P2

(12) United States Plant Patent
Olesen et al.

(10) Patent No.: US PP16,077 P2
(45) Date of Patent: Nov. 1, 2005

(54) MINIATURE ROSE PLANT 'POULRA016'

(50) Latin Name: *Rosa hybrida*
Varietal Denomination: POULra016

(75) Inventors: L. Pernille Olesen, Fredensborg (DK); Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 274 days.

(21) Appl. No.: 10/260,874

(22) Filed: Sep. 27, 2002

(51) Int. Cl.[7] ..... A01H 5/00
(52) U.S. Cl. ..... Plt./122
(58) Field of Search ..... Plt./122, 116, 129

*Primary Examiner*—Anne Marie Grunberg
*Assistant Examiner*—June Hwu

(57) ABSTRACT

A new miniature rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULra016'.

SUMMARY OF THE INVENTION

The present invention constitutes a new and distinct variety of miniature rose plant which originated from a controlled crossing between an un-named seedling 97/7472-6, created by the same inventors and an un-named seedling 95/5166-1, created by the same inventors. The two parents were crossed and the resulting seeds were planted in a cotrolled environment. The new variety is named 'POULra016'.

The new rose may be distinguished from its seed parent, an un-named seedling 97/7472-6, by the following combination of characteristics:

1. The un-named seedling 97/7472-6 has larger flowers;
2. The un-named seedling 97/7472-6 grows to be a larger plant;

The new variety may be distinguished from its pollen parent, a seedling 95/5166-1 created by the same inventors, by the following combination of characteristics:

1. The seedling 95/5166-1 has larger flowers;
2. The seedling 95/5166-1 grows to be a larger plant;

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra016' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULra016' was selected by the inventors as a single plant from the progeny of the hybridization in May, 1999.

Asexual reproduction of 'POULra016' by cuttings and traditional budding was first done by L. Pernille and Mogens N. Olesen in their nursery in Fredensborg, Denmark in August, 1999. This initial and other subsequent propagations conducted in controlled environments have demonstrated that the characteristics of 'POULra016' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra016'. Specifically illustrated in FIG. 1:

FIG. 1.1 Stem showing branching and the attachment of buds, peduncles, and flowers and open flower;

FIG. 1.2 Flower bud closed, partially open as sepals unfold, and a flower ¼ open;

FIG. 1.3 Flower petals, detached;

FIG. 1.4 Sepals, receptacle, and pedicel,

FIG. 1.5 Leaves;

FIG. 1.6 Bare stem exhibiting thorns.

DETAILED DESCRIPTION OF THE VARIETY

The following is a description of 'POULra016', as observed in its growth in a field nursery in Jackson County, Oreg. Color references are made using The Royal Horticultural Society (London, England) Colour Chart, 1995, except where common terms of color are used.

For a comparison, several physical characteristics of the rose variety 'POULhappy', a rose variety from the same inventors described and illustrated in U.S. Plant Pat. No. 9,483 and issued on Mar. 26, 1996 are compared to 'POULra016' in Chart 1.

CHART 1

| | 'POULra016' | 'POULhappy' |
|---|---|---|
| Color of upper surface of petal | Red Group 43A | Red Group 46B. |
| General tonality | Red Group 43A | Red Group 46B. |
| Petalage | 17–20 petals. | 25–30 petals. |

Parents: An un-named seedling 97/7472-6, and an un-named seedling 95/5166-1.

Classification:

*Botanical.*—*Rosa hybrida.*

*Commercial.*—Miniature.

FLOWER AND FLOWER BUD

Blooming habit: Nearly continuous.

Flower bud:

*Size.*—Upon opening, 30 mm–35 mm in length from base of receptacle to end of bud. Short.

*Bud form.*—Pointed ovoid.

*Bud color.*—As sepals unfold, Red Group 45A. At ¼ opening, Red Group 45A.

*Sepals.*—Upper surfaces of sepals are Green Group 144B with intonations of Greyed-Red Group 182A–B; lower surfaces of sepals are Green Group 144B with intonations of Greyed-Red Group 182A–B. Weak foliaceous appendages on three of the five sepals. Surfaces of sepals moderately pubescent. Stipitate glands are present on the edges and undersides of the sepals. Shape: Sepal apex is cirrose. Base is flat at union with peduncle. Size: 25 mm long×7–8 mm wide.

*Receptacle.*—Surface: Glaucous. Shape: Funnel. Size: 5 mm (h)×5 mm (w). Color: Green Group 144B.

*Pedicel.*—Surface: Limited numbers of stipitate glands present. Length: 44 mm to 48 mm average length. Color: Green Group 144B. On plants grown under high light conditions, pedicel may exhibit intonations of Greyed-Red Group 181B. Strength: Upright and moderately strong.

*Borne.*—With 1–4 buds per flowering stem.

*Anthocyanin.*—On plants grown under high light conditions, intonations of Greyed-Red Group 181B.

Flower bloom:

*Fragrance.*—Light.

*Duration.*—As a pot plant, flowers last from 22–28 days. The blooms have a duration on the plant of approximately 16–22 days. Petals fall cleanly away from plant.

*Size.*—Medium in size for a 8–11 cm floral pot rose. Average flower diameter is 55 mm when open.

*Form.*—Shape of flower when viewed from the side: Upon opening, upper part: Flat. Upon opening, lower part: Concave. Open flower, upper part: Convex. Open flower, lower part: Concave.

*Petalage.*—Average range: 17–20 petals under normal conditions with 4–6 petaloids.

Color:

*Upon opening, petals.*—Outermost petals: Outer Side: Red Group 44B. Inner Side: Red Group 44B. Innermost petals: Outer Side: Red Group 44B. Inner Side: Red Group 44B.

*Upon opening, basal petal spots.*—Outermost petals: Outer Side: White Group 155C with streak of Green-Yellow Group 1C. Inner Side: White Group 155C with streak of Green-Yellow Group 1C. Innermost petals: Outer Side: White Group 155C with streak of Green-Yellow Group 1C. Inner Side: White Group 155C with streak of Green-Yellow Group 1C.

*After opening, petals.*—Outermost petals: Outer Side: Red Group 43A. Inner Side: Red Group 43A. Innermost petals: Outer Side: Red Group 43A. Inner Side: Red Group 43A.

*After opening, basal petal spots.*—Outermost petals: Outer Side: White Group 155C with streak of Green-Yellow Group 1C. Inner Side: White Group 155C with streak of Green-Yellow Group 1C. Innermost petals: Outer Side: White Group 155C with streak of Green-Yellow Group 1C. Inner Side: White Group 155C with streak of Green-Yellow Group 1C.

*General tonality.*—On open flower Red Group 44A. No change in the general tonality at the end of the $5^{th}$ day. Afterwards, general tonality is Red Group 43A.

Petals:

*Petal reflex.*—Slight downward reflex.

*Petal edge.*—Petal edge is entire.

*Shape.*—Obovate.

*Petaloids.*—Quantity: 4–6 petaloids. Size: 7–10 mm long; 4–5 mm wide. Color: Red Group 44A on both the upper and lower surfaces.

*Thickness.*—Thin.

*Arrangement.*—Not formal.

Reproductive organs:

*Pistils.*—Length: 10 mm long. Quantity: 25–30.

*Pollen.*—Color: Yellow Group 13A. Quantity: Scant.

*Anthers.*—Size: 7 mm long. Color: Yellow Group 10B. Quantity: 40.

*Filaments.*—Color: Yellow Group 4C with intonations of Red-Purple Group 58B. Length: 4–6 mm.

*Stigmas.*—Slightly superior in location to anthers. Color: Green-White Group 157A.

*Styles.*—Color: Red-Purple Group 57B immediately below the stigma. Also, with intonations of Green-Yellow Group 1C.

*Seed formation.*—Not observed.

PLANT

Plant growth: Vigorous, compact, upright to bushy. When grown as a 8–11 cm pot plant, the average height of the plant itself is 18–22 cm and the average width is 24–26 cm. When grown as a nursery plant on its own roots the average plant height is 22–24 cm and the average plant width is 24–26 cm.

Stems:

*Color.*—Young wood: Yellow-Green Group 144B. Older wood: Yellow-Green Group 144D.

*Prickles.*—Incidence: 4–5 per 10 cm of stem. Size: Average length: 5 mm. Color: Greyed-Red Group 184D. Shape: Linear.

*Surface.*—Young wood: Smooth. Older wood: Rough.

Plant foliage: Normal number of leaflets on normal leaves in middle of the stem: 5 leaflets.

*Leaf size.*—75–80 mm (l)×50 mm (w).

*Quantity.*—Average to above average abundance.

*Color.*—Upper Leaf Surface: Green Group 146A. Lower Leaf Surface: Green Group 146C. Juvenile foliage: Upper Leaf Surface: Green Group 146A. Lower Leaf Surface: Green Group 146C. Anthocyanin intonation: Location: On plants grown under high light conditions; leaf margins of developing leaves, undersides of developing leaves, leaf rachis, flower peduncles, stems, and stipule edges may exhibit intonations of Greyed-Red Group 181A.

Plant leaves and leaflets:

*Stipules.*—Size: 20 mm (l)×6 mm (w). Color: Green Group 144B and C. On plants grown under hight light conditions, stipul edges may exhibit intonations of Greyed-Red Group 181A. Presence of stipitate glands: Edges. Anthocyanin: Greyed-Red Group 181A.

*Petiole.*—Length: 10 mm. Color: Green Group 144B. Underneath: Green Group 144B. Margins: Green Group 144A. Anthocyanin: On plants grown under high light conditions, petioles may exhibit intonations of Greyed-Red Group 181A.

*Rachis.*—Color: Green Group 144A. Underneath: Green Group 144B. Margins: Green Group 144B. Anthocyanin: On plants grown under high light conditions, leaf rachis may exhibit intonations of Greyed-Red Group 181A.

*Leaflet.*—Edge: Serrated. Shape: Ovate. Texture: Glossy finish. Thin. Arrangement: Odd pinnate. Venation: Reticulate.

Disease resistance: Average resistance to mildew, black spot, and *Botrytis* under normal growing conditions in Jackson County, Oreg.

We claim:

1. A new and distinct variety of rose plant of the miniature class, substantially as herein illustrated and described as a distinct and novel rose variety due to its abundant, red flowers, vigorous growth, compact habit, suitability for production from softwood cuttings in pots, and durable flowers and foliage which make the variety suitable for distribution in the floral industry.

* * * * *

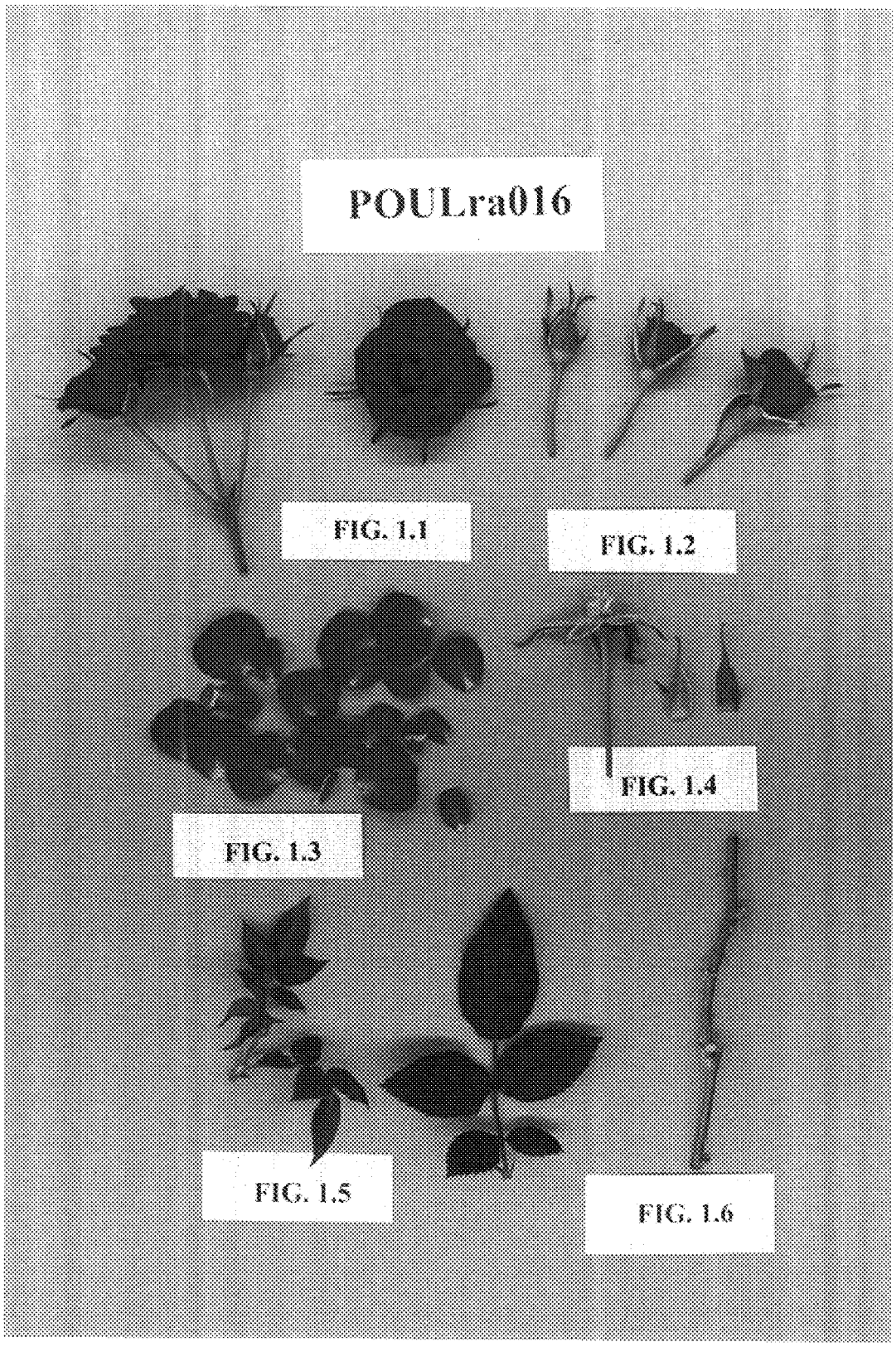
POULra016
FIG. 1.1
FIG. 1.2
FIG. 1.3
FIG. 1.4
FIG. 1.5
FIG. 1.6